(12) United States Patent
Westin

(10) Patent No.: US 6,386,027 B1
(45) Date of Patent: May 14, 2002

(54) METHOD AND DEVICE FOR MEASURING Z-DIRECTIONAL TENSILE STRENGTH OF PAPER OR BOARD

(75) Inventor: Dennis Westin, Kista (SE)

(73) Assignee: AB Lorentzen & Wettre, Kista (SE)

(*) Notice: Subject to any disclaimer, the term of this patent is extended or adjusted under 35 U.S.C. 154(b) by 0 days.

(21) Appl. No.: 09/251,912

(22) Filed: Feb. 19, 1999

(30) Foreign Application Priority Data

Feb. 25, 1998 (SE) .............................................. 9800569

(51) Int. Cl.$^7$ ................................................ G01L 5/04
(52) U.S. Cl. ........................................................ 73/159
(58) Field of Search .......................... 73/159, 73, 95.5, 73/150 A, 847, 830; 162/358.5

(56) References Cited

U.S. PATENT DOCUMENTS

| | | | |
|---|---|---|---|
| 3,757,574 A | * 9/1973 | Plankinton | ................. 73/150 A |
| 3,838,596 A | 10/1974 | Neuenschwander | |
| 3,927,558 A | * 12/1975 | Phillippe et al. | ................. 73/95 |
| 5,297,062 A | * 3/1994 | Cresson et al. | ............. 364/564 |
| 5,964,973 A | * 10/1999 | Heath et al. | ................. 156/161 |

FOREIGN PATENT DOCUMENTS

| EP | 0200650 | 12/1986 |
|---|---|---|
| EP | 0348177 | 12/1989 |

OTHER PUBLICATIONS

T 541 om–89. Internal bond strength of paperboard ($z_{di}$-rection tensile) (1988).

\* cited by examiner

Primary Examiner—Benjamin R. Fuller
Assistant Examiner—Octavia Davis
(74) Attorney, Agent, or Firm—Browdy and Neimark, P.L.L.C.

(57) ABSTRACT

A method of measuring the z-directional tensile strength of a sample (2) of paper or board in a direction perpendicular to its surface by coating the sample (2) on the two opposite surfaces with double-sided pressure-sensitive adhesive tape (5, 5') so as to obtain a sandwich structured sample web (3); bringing, on each of the two opposite sides of the sample web (3), a tensile strength tester platen (10, 10') in contact with the free surface of the double-sided pressure-sensitive adhesive tape (5, 5'); fastening, on each of the two opposite sides of the sample web (3), the tensile strength tester platen (10, 10') to the free surface of the double-sided pressure-sensitive adhesive tape (5, 5'); pulling apart the tensile strength tester platens (10, 10') by use of a tensile force; and measuring the tensile force necessary to break the sample (2) in a plane between its opposite surfaces; characterized in that a number of z-directional tensile strength tests may be performed at separate locations on a continuous sample web (3); as well as a device for performing the method, permitting extensive automatization of the z-directional tensile strength testing procedure.

20 Claims, 8 Drawing Sheets

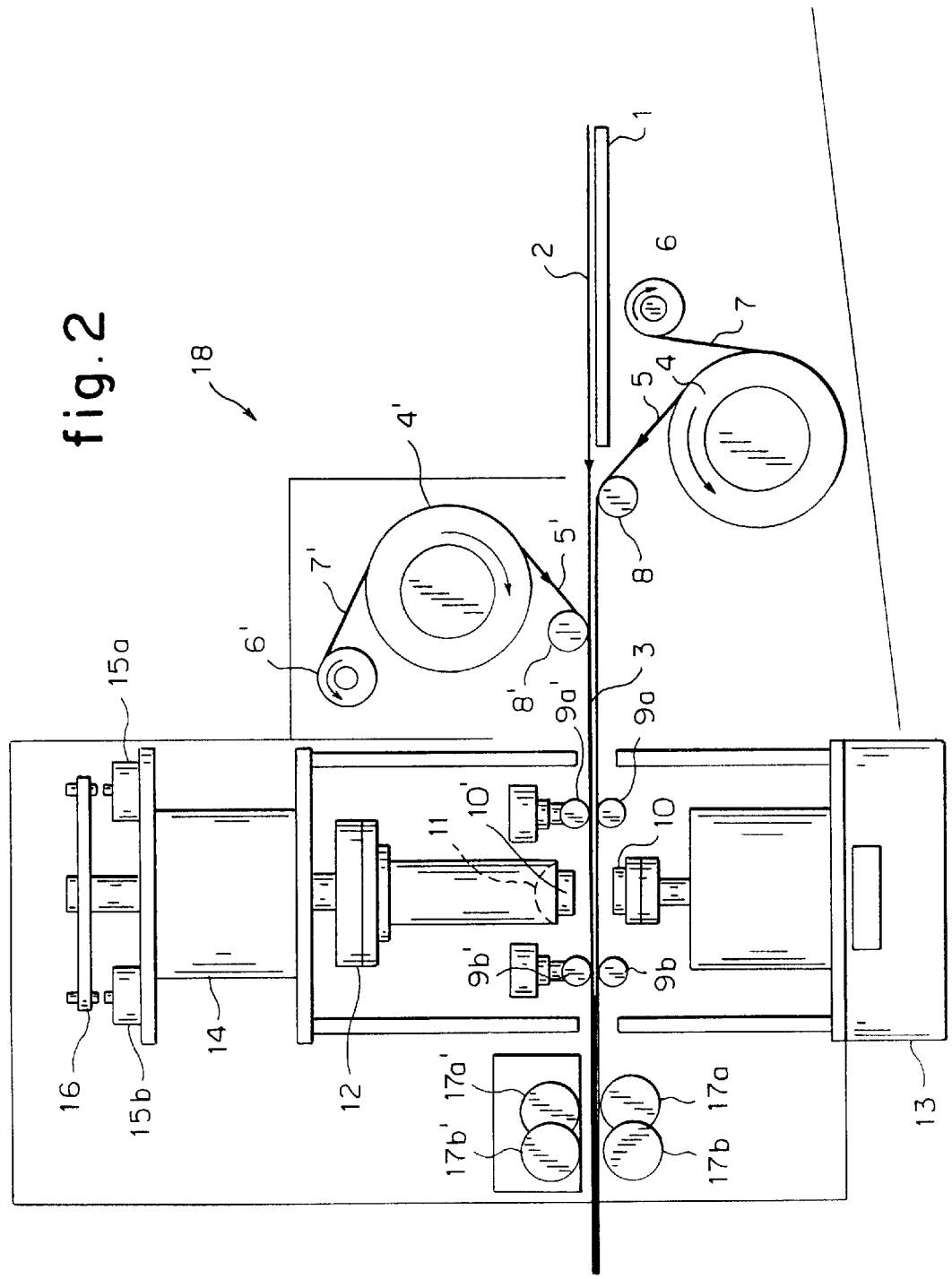

METHOD AND DEVICE FOR MEASURING Z-DIRECTIONAL TENSILE STRENGTH OF PAPER OR BOARD

This invention relates to a method of measuring the z-directional (out of plane) tensile strength of paper or board, as well as to a device applicable in such a method.

BACKGROUND OF THE INVENTION

The z-directional tensile strength of a paper or board, i.e. the internal tensile strength thereof in a direction perpendicular to its surface, the thickness direction, may be defined as the maximum tensile stress at break of a defined test area of the material in a plane between its upper and lower surface when loaded in an out of plane mode under defined standard conditions.

There is a multitude of terms referring to the tensile strength in the z-direction of a paper or board. Depending on the method and purpose of measurement as well as the type of sample tested, terms such as z-directional tensile strength, Scott Bond, internal bond strength, internal fiber bond strength, ply adhesion and ply bond strength have been used.

The z-directional tensile strength of a paper or board is for many reasons a critical parameter thereof, which often has to be specified by the manufacturer. By way of example, in processes of applying coatings such as sizings or printing inks to a sheet of paper or board, too low a value of the z-directional tensile strength may lead to the pulling apart of the sheet by adhesion to the applicator, such as a roll, causing build-up thereon of the paper or board.

Also, out of environmental concern there is an increasing demand for recycled paper fibre. However, the higher the content of recycled fibre is in the paper or board, the more difficult it is to obtain an adequate bonding together of the internal layers of the material and thus the more difficult it is to obtain a satisfactory tensile strength. In this case, to ensure a high quality material, frequent controls of the z-directional tensile strength are necessary.

Too high a z-directional tensile strength may also cause problems, since this may lead to inadequacy of other properties of the paper or board, such as folding stiffness or tear strength.

In view of the importance of the z-directional tensile strength as a quality parameter of a paper or board, standards have been developed for its testing, as well as devices applicable in such testing.

In the United States, the standard for testing the z-directional tensile strength of paperboard is given in TAPPI 541, as described in T 541 om-89, incorporated herein by reference and which may be found in TAPPI TEST METHODS 1996–1997, ISBN no. 0–89 852–334–6, ed. TAPPI PRESS, Atlanta, US. The testing procedure consists of applying double (two-sided) coated, pressure-sensitive tape to both sides of a test piece. The test piece then is placed between two platens and compressed uniformly over the entire test area. Finally, uniform tension is applied over the entire test area in a direction perpendicular to the plane of the test piece (z-direction) to effect a separation.

As defined in the TAPPI 541 standard, the testing apparatus comprises a z-direction tensile-compression tester; double (two-sided) coated pressure sensitive tape, 50 mm wide; paper cutters or scissors; and 10 kg calibration weights. The tensile-compression tester is equipped with a force measuring device of 90 kg minimum capacity; 6.45 cm$^2$ tester platen area and a self-adjusting test head (which compensates for any lack of surface parallelism), and provides for a test cycle consisting of a compression stroke, a dwell time (to assure an adequate tape bond between the test piece and the tester platens) and a tension stroke (which effects the splitting of the material, leaving a portion of the material on each of the tester platens). The complete test cycle requires approximately 45 seconds.

A tensile-compression tester conforming to the TAPPI 541 standard is sold by Testing Machines Inc., of the USA, under the name of Monitor/ZD™.

In the Scandinavian countries, the Scandinavian Pulp, Paper and Board Testing Committee recently has put forward a new standard for the testing of the z-directional tensile strength. This standard is to be published in 1998 and will be referred to as SCAN P80:98. In its basic principle, the new standard conforms to the TAPPI 541 standard, however with different values of testing parameters such as the test area and the compression force. Said standard as published is incorporated herein by reference.

Thus, the apparatus according to the proposed Scandinavian standard comprises a compression device with a compression force of (3±0.5 MPa); a tensile apparatus; two flat circular tester platens having a test surface area of (10±0.1 cm$^2$); a device for aligning the tester platens; self adhesive tape, double (twosided) coated; punch or cutter for preparation of test pieces; and solvent.

The test pieces, with a diameter of at least 50 mm or, if square, no side shorter than 50 mm, according to this standard is to be cut from specimens of undamaged paper or board.

The detailed procedure starts with the cleaning of the tester platens with a solvent such as ethyl alcohol or similar prior to each day's testing. It is of uttermost importance that the test surface of the platens then be maintained perfectly clean.

Next, the protective liner is removed from one side of pieces of the double (two-sided) coated self adhesive tape which are then applied to each side of the test piece. The other protective liner then is removed from the adhesive tape on each side of the test piece, and the whole sandwich structured test piece is placed between the aligned tester platens so that the test piece protrudes outside the tester platens by at least 4 mm around the whole circumference. The whole assembly of tester platens and test piece is placed in the testing apparatus comprising a compression and tensile device, a force sensor as well as self-adjusting heads compensating for any lack of parallelism of the tester platens and the test piece.

After the test area has been compressed with a specified compression force during a specified dwell time between the platens, it is strained to break; the recorded maximum force corresponds to the z-directional tensile strength.

When finally removing the test piece from the tester platens, care should be taken not to touch the test surface of the platens, or else the surface has to be cleaned again with solvent and dried.

A tensile-compression tester conforming to the proposed Scandinavian standard is sold by Lorentzen and Wettre, under the name of Alwetron™.

According to this standard, at least 5 determinations should be performed to get a statistically significant result.

From the above description of the testing method it will be apparent that in order to obtain a reliable value of the z-directional tensile strength, quite cumbersome testing procedures have to be performed involving a substantial amount of manual work comprising the cutting to pieces of the material to be tested and of the adhesive tape, the mounting and taking apart of the test assembly comprising the tested material, the tape and the tester platens. Moreover, it is in fact often not easy to avoid touching the surface of the platens in order to remove every trace of residue after a test, and consequently, frequently the use of a solvent is required in order to clean the tester platen surface from e.g. hand grease, which is a drawback from an environmental point of view as well as a health hazard to the person performing this cleaning, being exposed to the solvent.

Moreover, the manual application of the adhesive tape to the material not always is devoid of difficulties, such as forming of wrinkles in the tape. A test piece bearing an imperfectly applied tape has to be discarded.

Thus, the testing method, due to the large amount of manual work, is quite slow, being both cumbersome and time-consuming, whereas the production of the paper or board in itself is a fast process.

Consequently, there is a need for a method of testing the z-directional tensile strength of paper or board, as defined in the above standards, fulfilling the requirements of being faster and more easily performed by involving less of manual operations as well as providing accurate z-directional tensile strength values in a repeatable way.

It is an object of the present invention to meet said need.

GENERAL DESCRIPTION OF THE INVENTION

For the purpose of the invention the following terms will have the meaning as defined herein below:

Test area: the surface area whereupon the z-directional tensile strength test is performed, i.e. corresponding to the test surface area of the tester platen. E.g. according to the TAPPI standard the test area is 6.45 $cm^2$ whereas according to the SCAN standard it is 10 $cm^2$.

Test piece: a piece of paper or board originating from a sheet of paper or board, e.g. from a jumbo roll produced in a paper mill, whereupon a number of z-directional tensile strength tests are to be performed.

Sample: a number of $n \geq 1$ test pieces, which, in case n>1, are assembled in a sequence so as to give a piece of greater length, whereupon a number of z-directional tensile strength tests are to be performed. Obviously, a test piece is equivalent to a sample having n=1.

Sample web: a sandwich structure consisting of a test piece (n=1) or a sample ($n \geq 1$) having double-sided pressure-sensitive adhesive tape applied to both sides.

The object of the invention is achieved by a method and a device for measuring the z-directional tensile strength as defined in the appendant claims.

The method of measuring the z-directional tensile strength of a sheet of paper or board according to the invention is essentially characterized in that a number of z-directional tensile strength tests may be performed at separate locations on a continuous sample of the sheet, using a sample which permits the carrying out of a number of z-directional tensile strength tests.

According to a preferred feature of the method of the invention, after performing a tensile strength test on a sample web by use of a device of the invention comprising a tensile strength testing apparatus with a pair of tester platens, the tester platens are detached from the sample web while the sample web is retained by the grip of holding means.

According to another preferred feature of the method of the invention, after detaching the tester platens from a test area of the sample web on which a z-directional tensile strength test has been performed, a following section of the sample web is fed into the space between the tester platens.

According to still another preferred feature of the method of the invention, any imperfect parallelism between the tester platens and the sample web when bringing the tester platens in contact with the sample web is compensated for.

According to another preferred feature of the method of the invention, the sample of paper or board to be tested may comprise a sequence of several test pieces attached to each other.

The inventive method is performed by use of the device of the invention, which is essentially characterized in that it comprises means for delivering double-sided pressure-sensitive adhesive tape provided with protective liner on at least one side, means for removing the protective liner from the double-sided pressure-sensitive adhesive tape; means for applying the double-sided pressure-sensitive adhesive tape to each side of a sample of paper or board to be tested, giving a sandwich structured sample web formed of the sample on both sides coated with the double-sided pressure-sensitive adhesive tape; means for feeding the sample web into a z-directional tensile strength tester; a z-directional tensile strength tester comprising a pair of tester platens, of which at least one is mobile in a direction essentially perpendicular to the plane of the test surface the other tester platen to come in contact with the sample web; and means for retaining the sample web, provided on each side of the tensile strength tester.

According to a preferred feature of the device of the invention, the means for feeding the sample web are located on each side of the plane of the sample web, at the exit side of the tensile strength tester.

According to another preferred feature of the device of the invention, the means for removing the protective liner from the pressure-sensitive adhesive tape and the means for applying the pressure-sensitive adhesive tape to the sample, to form a sample web, are located on each side of the plane of feeding of the sample web.

According to still another preferred feature of the device of the invention, means are provided to compensate for any imperfect parallelism of the alignment of the surface of the sample web and the tester platens, respectively.

According to still another preferred feature of the device of the invention, the device is coupled to means for controlling the device and for receiving, storing and treating input as well as output data.

The invention provides an extensively automatized method and device wherein the cutting of the test piece of paper or board is simple to perform and non-critical to the test result; the double-sided pressure-sensitive adhesive tape is automatically applied to both sides of the sample, giving a sample web, which is automatically fed into the tensile strength tester; the tester platens are automatically applied to both sides of the sample web; and the z-directional tensile strength is automatically measured with registration and optionally recording of the exerted force.

The method and device of the invention, by eliminating the cumbersome manual operations of the methods according to the state of the art, as a further beneficial effect will provide a measure of the z-directional tensile strength with a very high degree of accuracy and repeatability.

Moreover, due to the reduced manual handling of the tester platens in the method of the invention, the need of using a solvent to clean the tester platens is substantially reduced, which from an environmental and health protection point of view is very beneficial.

DETAILED DESCRIPTION OF THE INVENTION

The invention will now be illustrated by the description of a preferred embodiment thereof, with reference to the drawings wherein:

FIG. 2 is a schematic view of a device according to the invention; and

Figure 1A:
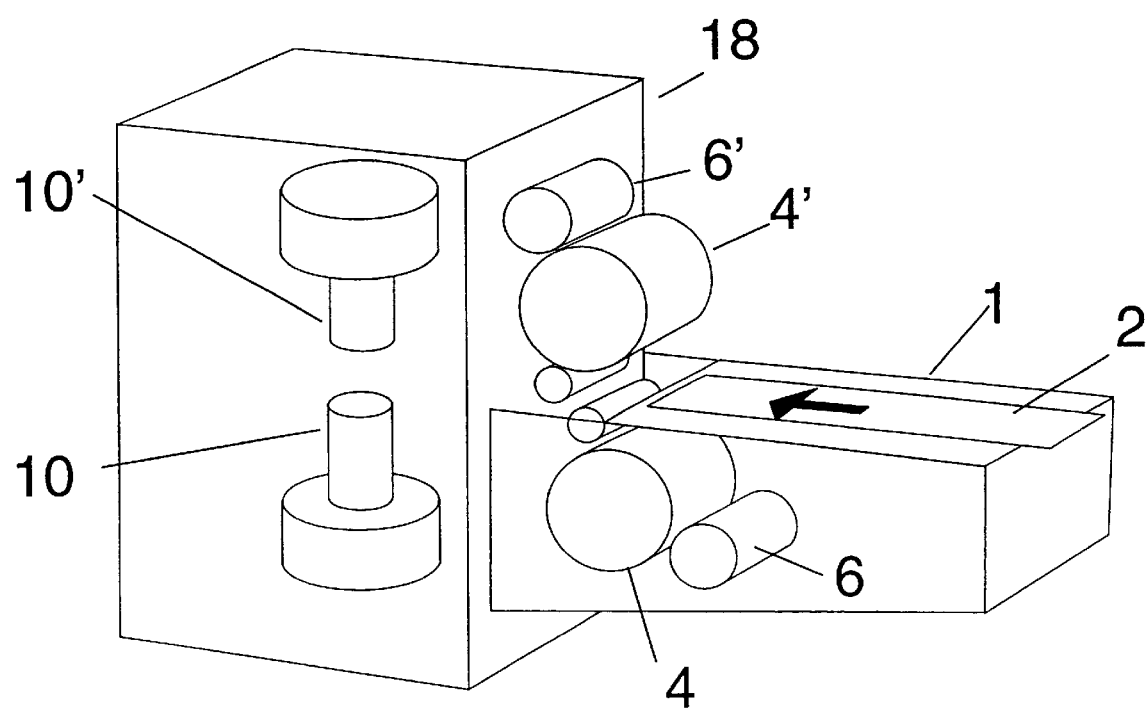
FIG. 1(a–f) is a schematic illustration of the principal steps of a procedure for measuring the z-directional tensile strength according to the method of the invention.

FIG. 1a corresponds to the first step of the procedure of the invention, which is the introduction of a sample 2 of paper or board into the device 18 of the invention.

Figure 1B:
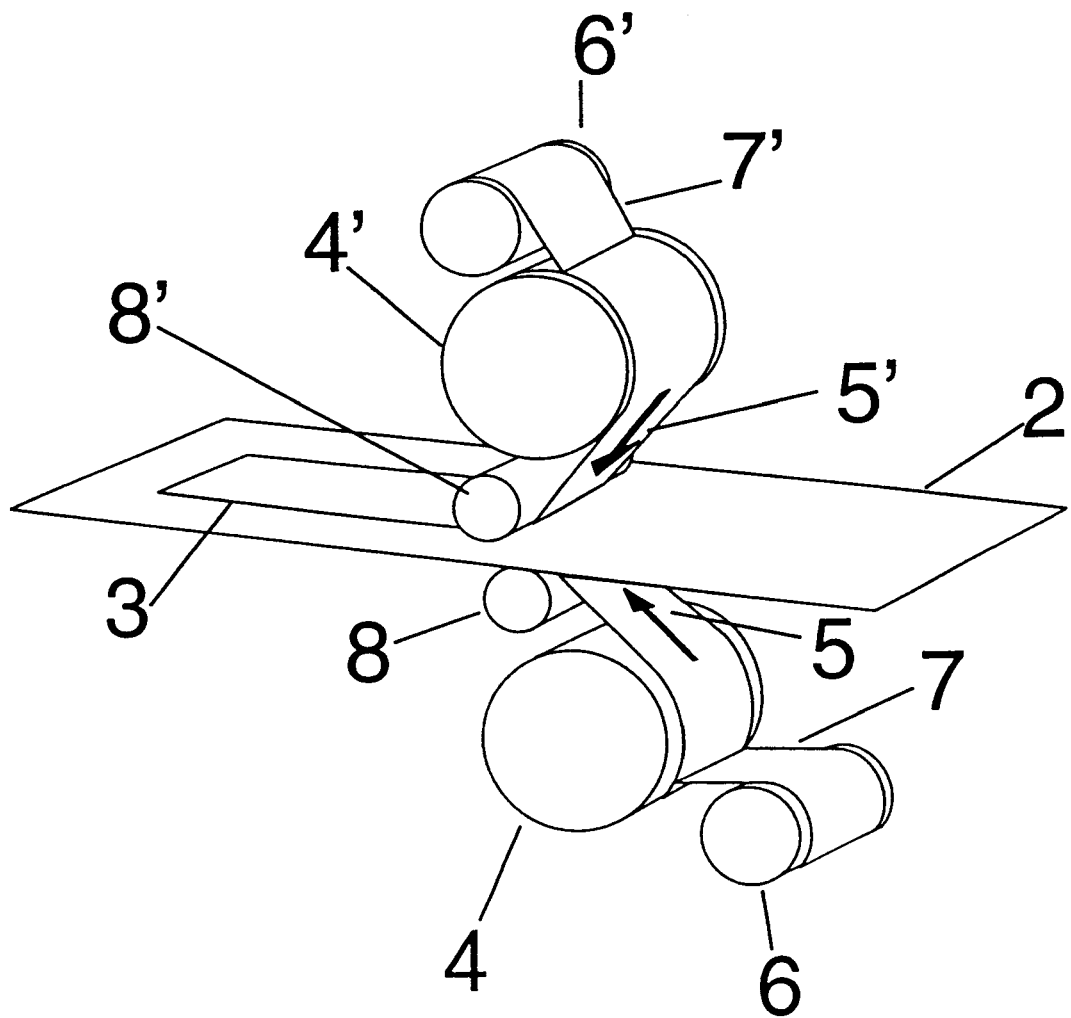

The second step, FIG. 1b, is the application of double-sided pressure-sensitive adhesive tape 5, 5' to both sides of the sample 2, forming a sample web 3 which is simultaneously fed forward in the device 18.

Figure 1C:
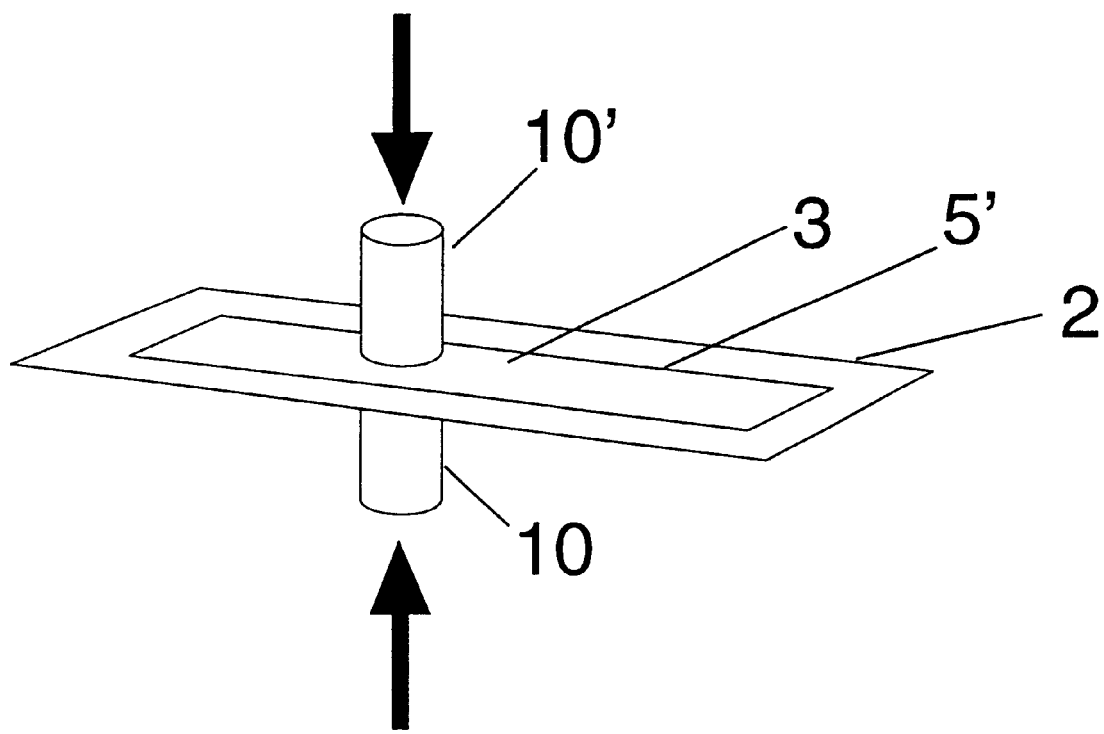

The third step, FIG. 1c, is the application of the tester platens 10, 10' to both sides of a test area of the sample web 3 which has entered the space between the tester platens 10, 10'.

Figure 1D:
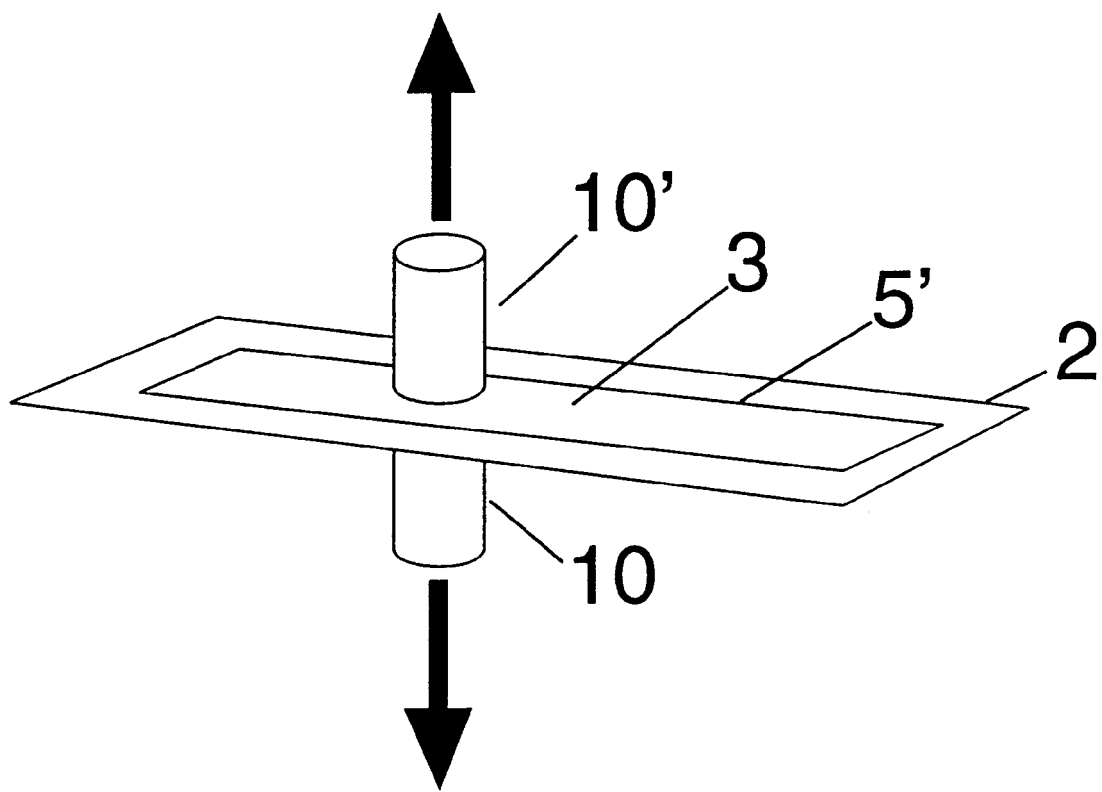

The fourth step, FIG. 1d, is the actual performance of the z-directional tensile strength test, by pulling apart the tester platens 10, 10' and recording the maximum tensile stress at break of the tested sample 2.

Figure 1E:
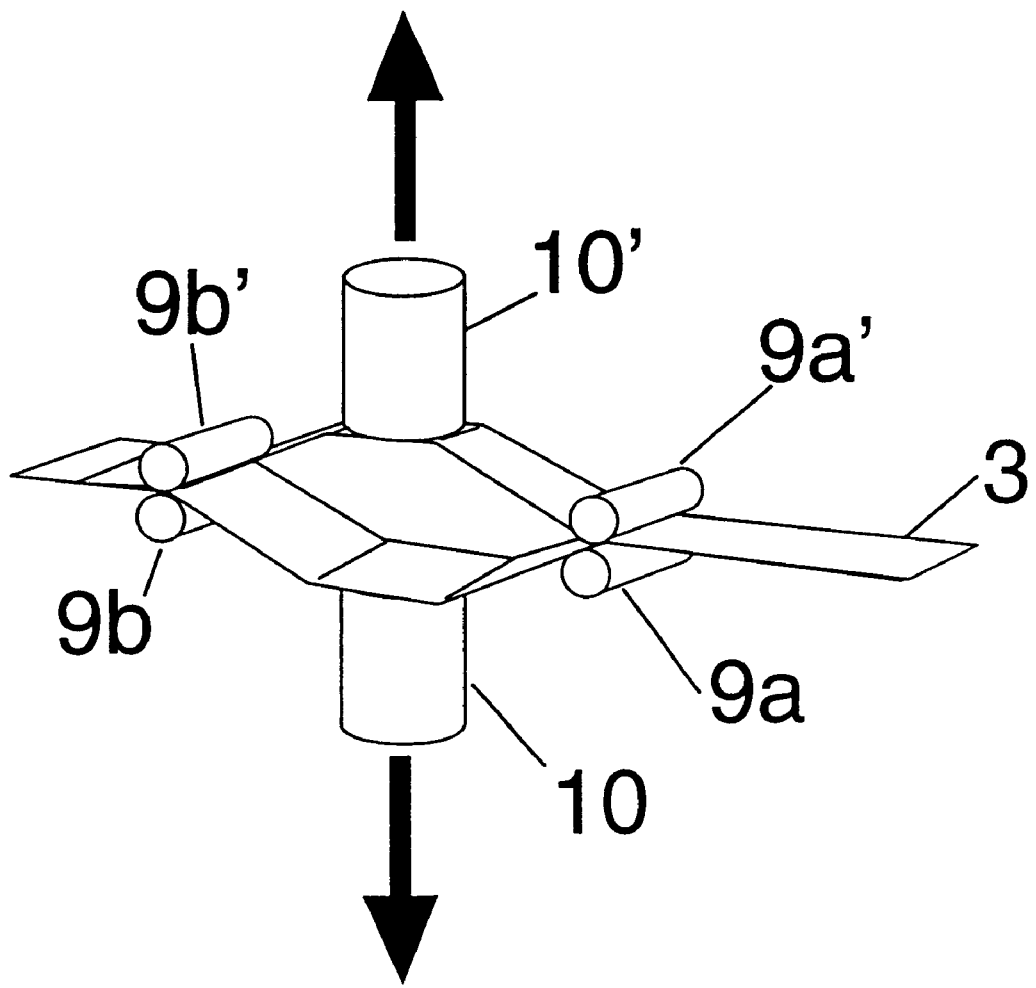

The fifth step, FIG. 1e, is the detachment of the tester platens 10, 10' from the sample web 3.

Figure 1F:
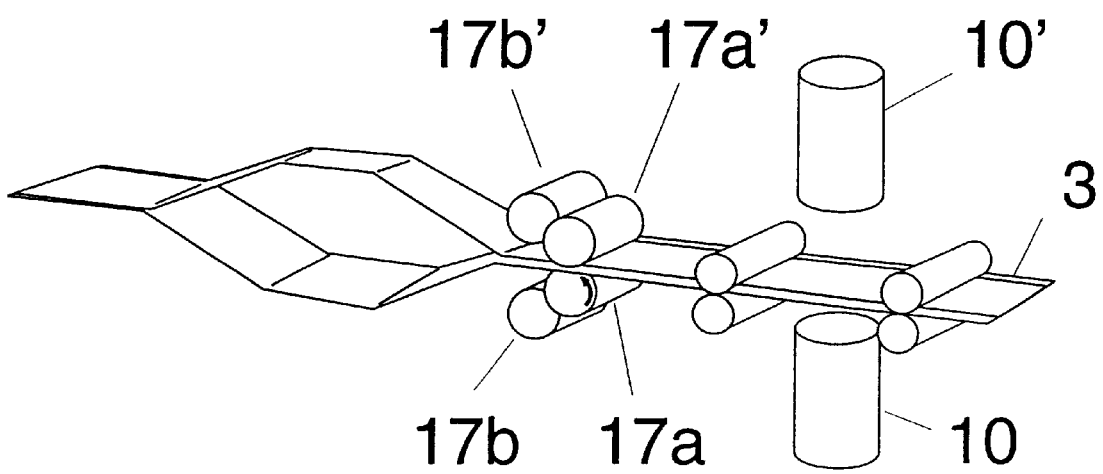

The sixth step, FIG. 1f, is the further feeding of the sample web 3, whereby a non-tested test area of the sample web 3 enters the space between the tester platens 10, 10' while the previously tested test area thereof exits at the opposite side.

The device 18 as represented in FIG.2 will be described starting from the right side on the drawing and proceeding to the left, in correspondence with the sample web 3 feed direction in the device 18 according to the drawing. The device 18 comprises a feeder table 1 for a sample 2 of paper or board to be tested in the form of a sample web 3 and, on each side of the horizontal plane formed by the sample web 3, i.e. the feeding plane thereof, rolls 4, 4' of double-sided pressure-sensitive adhesive tape 5, 5' provided with protective liner 7, 7' on at least one side. In association with each roll 4, 4' of pressure-sensitive adhesive tape 5, 5', a peel-off roll 6, 6' for the protective liner 7, 7' of the double-sided pressure-sensitive adhesive tape 5, 5' is provided. On each side of the horizontal plane formed by the sample web 3, a deflection roll 8, 8' for the double-sided pressure-sensitive adhesive tape 5, 5' is provided. At the inlet side of the main part of the device 18, i.e. the tensile strength testing apparatus per se, or tensile strength tester, one pair of lower and upper holding rolls 9a, 9'a is provided, a similar pair of holding rolls 9b, 9b' being provided on the outlet side thereof.

The tensile strength testing apparatus per se, or tensile strength tester, comprises a pair of tester platens 10, 10' of which the upper one 10' at its end proximal to the plane of the sample web 3 comprises a hemispherical bearing 11; a force sensor 12; pneumatic cylinders 13, 14, 15a, 15b and a lifting yoke 16.

Following the holding rolls 9b, 9b' on the outlet side of the tensile strength tester, two pairs of feeding rolls 17a, 17b; 17a', 17b' are provided, one pair on each side of the horizontal plane formed by the sample web 3.

Figure 3:
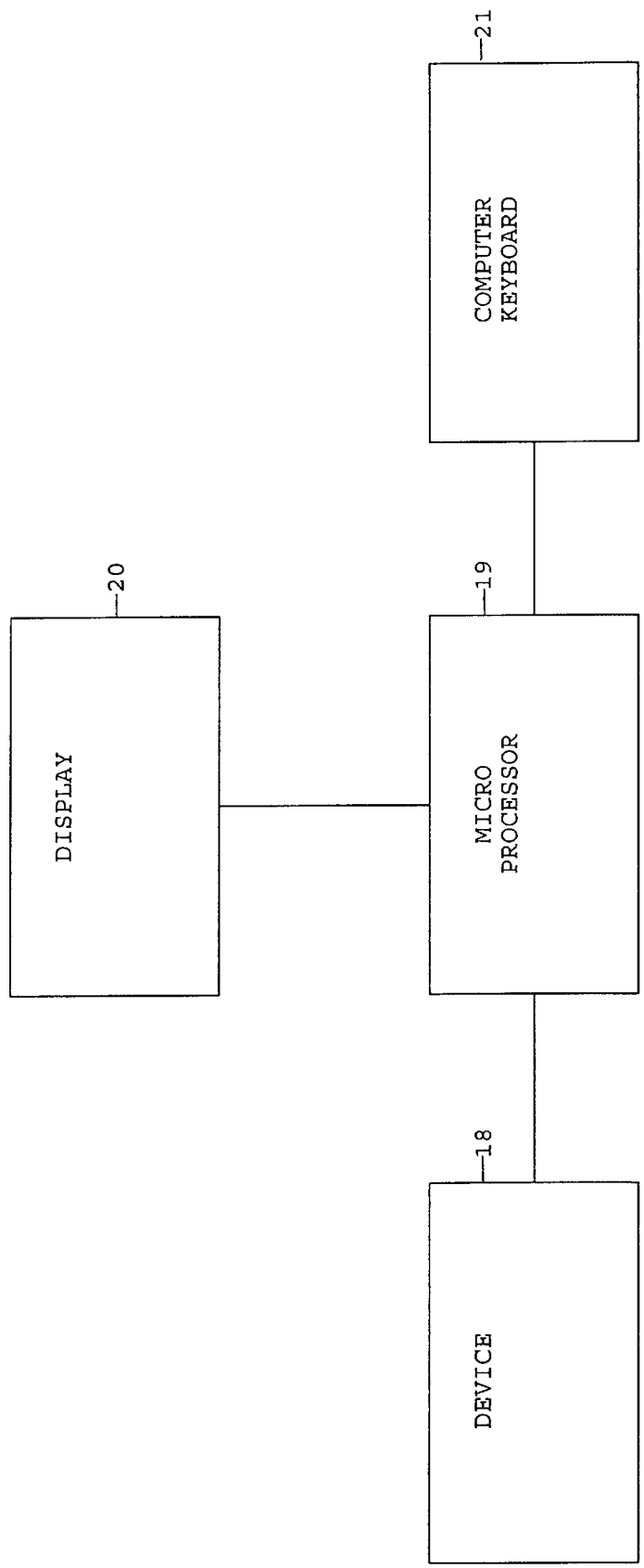
FIG.3 is block diagram schematically illustrating a device according to the invention coupled to an electronic unit.

The device 18 of the invention in a preferred embodiment is coupled to an electronic unit, as schematically represented in FIG. 3, of a conventional character to control the device 18 and to receive, store and treat input as well as output data. This unit typically comprises microprocessors 19, a display unit 20 to present the results and to be able to see the communication with the computer program in the microprocessors 19 and a computer keyboard 21 to communicate with the computer program and to be able to start the testing operation.

Also comprised in the device 18 of the invention, but not represented in the figures, are magnetic valves actuating the pneumatic cylinders 13, 14, 15a, 15b on command from the computer program.

The microprocessors 19 of the electronic unit contain a computer program to control the measuring sequence and to receive and interpret the signal from the force sensor 12 as well as to receive the operator input from the computer keyboard 21. The computer program may also control the display 20 presenting measured data.

At the computer keyboard 21, those parameters may be changed which it is desired to modify as a function of the quality of the paper or board to be tested, e.g. the distance between separate test areas; the number of tests to be performed on a given sample, the length of a given sample; the number of test pieces, that the sample will possibly comprise; the compression force and dwell time to be used; the force incremental increase by unit of time at the tensile strength testing; the form of the data output e.g. averaged or not averaged data; statistical parameters to be presented, such as standard deviation and coefficient of variation; destination of output data, e.g. whether or not they are to be sent to a main computer and whether or not they are to be sent to a printer; etc.

After having performed a selection of a number of parameters, these may be stored in the microprocessors 19 as a measuring sequence having a given program number. This measuring sequence then may be retrieved and used e.g. when a paper or board of similar quality is to be tested.

The method of the invention as outlined above with reference to FIG. 1A will now be described in further detail in association with the device 18 as disclosed herein above with reference to FIG. 2 and FIG. 3.

The sample 2 of paper or board to be tested is placed on the feeder table 1, with the left end of said sample proximal to and above the lower double-sided pressure-sensitive adhesive tape 5 that passes over deflection roll 8. The left end of the sample is then manually pressed down and fastened to the lower double-sided pressure-sensitive adhesive tape 5.

The measuring sequence is then started, preferably by giving a starting command to the microprocessor program with the computer keyboard 21. By way of the feeding rolls 17a, 17b; 17a', 17b' the lower and upper double-sided pressure-sensitive adhesive tapes 5, 5' and the sample 2 are drawn forward into the device.

As the sample 2 passes over the lower deflection roll 8, its lower surface is coated with the lower double-sided pressure-sensitive adhesive tape 5, the protective liner 7 of the lower double-sided pressure-sensitive adhesive tape 5 being simultaneously wound up around the lower peel-off roll 6.

As the sample 2, coated on its lower side with the lower double-sided pressure-sensitive adhesive tape 5, passes below the upper double-sided pressure-sensitive adhesive tape 5' below the upper deflection roll 8', its upper surface is coated with the upper double-sided pressure-sensitive adhesive tape 5', the protective liner 7' of the upper double-sided pressure-sensitive adhesive tape 5' being simultaneously wound up around the upper peel-off roll 6'. As a result, a sandwich structured sample web 3 is formed, consisting of the sample 2 on both sides coated with double-sided pressure-sensitive adhesive tape 5, 5'.

The sample web 3 is pulled forward by the feeding rolls 17a, 17b; 17a', 17b' until a test area thereof, on which the first test of the z-directional tensile strength of the sheet is to be performed, enters the space between the tester platens 10, 10'. The feeding of the sample web 3 then is interrupted by stopping the movement of the feeding rolls 17a, 17b; 17a', 17b'.

Pneumatic cylinder 13, by exerting a vertically upwards directed compression force on the lower tester platen 10, pushes it up to an extreme position in contact with the lower double-sided pressure-sensitive adhesive tape 5 on the lower surface of the sample web 3.

Next, the upper tester platen 10' is pushed downward by a compression force exerted by pneumatic cylinder 14 until it enters into contact with the upper double-sided pressure-sensitive adhesive tape 5' on the upper surface of the sample web 3.

The hemispherical bearing 11 of the upper tester platen 10' will provide a compensation for any lack of parallelism of the sample web 3 and the test surface of the tester platens 10, 10' when bringing the tester platens 10, 10' in contact with the sample web 3. The centre of rotation of bearing 11 is located close to the centre of the sample web 3 test area. This will allow adjustment of the surface of the tester platens 10, 10' while the vertical symmetry axes of the tester platens 10, 10' respectively in the pneumatic cylinders 13, 14 remain immobile and in perfect vertical alignment with each other.

By a normalized compression force exerted by the pneumatic cylinder 14, the double-sided pressure-sensitive adhesive tapes 5, 5' on both sides are fastened to the test area of the sample 2 in the same time as the tester platens 10, 10' on both sides of the plane of the sample web 3 are fastened to the double-sided pressure-sensitive adhesive tape 5, 5', the pneumatic cylinder 13 acting as an abutment.

The compression force is activated during the time period specified in the used standard whereafter air is vented from the pneumatic cylinder 14 until no compression force is exerted on the test area of the sample web 3.

Next, pneumatic cylinders 15a, 15b are activated, and induce a slow upwards directed motion to the lifting yoke 16, which is coupled to the upper tester platen 10' through the force sensor 12.

The adhesive force between the double-sided pressure-sensitive adhesive tapes 5, 5' and the tester platens 10, 10' in association with the z-directional tensile strength of the sample 2 offer a resistance to the upward directed tensile force exerted by the pneumatic cylinders 15a, 15b.

As the lifting yoke 16 continues to move upwards, a point is reached where the z-directional tensile strength of the sample 2 no longer is sufficient to resist the tensile force induced, and there will be rupture in said sample 2 somewhere in between its upper surface in contact with the upper double-sided pressure-sensitive adhesive tape 5' and its lower surface in contact with the lower double-sided pressure-sensitive adhesive tape 5. The maximum value of the force registered by the force sensor 12 divided by the test area of the sample web 3 is the z-directional tensile strength of the sample 2.

When rupture of the sample 2 in the test area occurs, the upper tester platen 10' usually has moved upwards over a distance of only a few thousandths of millimeters, such as 0.005–0.01 mm. The stroke of the pneumatic cylinders 15a, 15b is adjusted to permit a total upward motion of the upper tester platen 10' at the moment of rupture of only a few millimeters, such as 1–3 mm.

Upon termination of the measuring sequence, the two pairs of holding rolls 9a, 9a'; 9b, 9b' are brought into contact with the sample web 3, gripping it on each side of the tensile strength tester.

The upper tester platen 10' is slowly drawn upwards by pneumatic cylinder 14, and simultaneously the lower tester platen is slowly drawn downwards by pneumatic cylinder 13. The sample web 3, being retained by the grip of holding rolls 9a, 9a'; 9b, 9b', will come off the tester platens 10, 10' as these move vertically away.

When the tester platens 10, 10' have reached their respective upper and lower extreme positions they thus will be free from any residue of the double-sided pressure-sensitive adhesive tape 5, 5' and sample 2 from the sample web 3.

The grip of the holding rolls 9a, 9a'; 9b, 9b' on the sample web 3 is released by bringing said rolls out of contact with the sample web 3, and the feeding of the sample web 3 is resumed, whereby the tested area thereof exits from the space between the tester platens 10, 10' while a following test area of the same sample web 3 enters this space, and a new test may be performed, this being repeated the desired number of times until the end of the sample web 3 is reached.

The material and design of the tester platens 10, 10', the feeding rolls 17a, 17a'; 17b, 17b' and the holding rolls 9a, 9a'; 9b, 9b' are selected so as to combine the characteristics of being able to give a good contact with the sample web 3 to provide a good grip thereon, and of being easy to detach from the sample web 3.

The material of the tester platens 10, 10' preferably is suitable for being polished to an adequate surface evenness and fineness. Said material should give an adequate adherence with the adhesive tape 5, 5', to be able to delaminate the sample 2 of the sample web 3 during the tensile strength testing. However, it should also be easy to remove the adhesive tape 5, 5' from the surface of the tester platens 10, 10', so as not to leave any residue thereon. As an example, a suitable material for the tester platens 10, 10' is stainless steel SS 142346.

The surface structure and material of the feeding rolls 17a, 17a'; 17b, 17b' should provide an adequate frictional force between said rolls and the sample web 3, to be able to perform the feeding thereof, while also allowing the sample web 3 to come off easily from said rolls at the exit side thereof. As an example, the feeding rolls 17a, 17a'; 17b, 17b' may comprise a number of SS 142346 stainless steel disks having a diameter of 30 mm and thickness of 2 mm, mounted on a central axis of rotation at intervals of 3 mm, i.e. 5 mm separation between the centres of adjacent disks. The disks preferably are knurled, i.e. the circumferential surface of each disk is serrated, providing both a high friction and a small contact surface towards the sample web 3, so as to ensure the required characteristics of good grip and easy detachment.

The arrangement of two consecutive pairs of lower and upper feeding rolls 17a, 17a'; 17b, 17b' will ensure that the adhesive tape come off said rolls at the exit side thereof. The horizontal distance between the axes of rotation of the two pairs of rolls, 17a, 17a' and 17b, 17b' respectively, is less than the sum of the radii of their respective constitutive disks, the rolls being so arranged that the disks of each roll in a pair of rolls will penetrate into the intervals separating the disks of the horizontally adjacent roll. In the case of the example where the diameter of all disks are 30 mm, at a horizontal distance of 25 mm between the first pair of feeding rolls 17a, 17a' and the second pair 17b, 17b' the disks of each one roll will penetrate by 5 mm, in the plane of the sample web, i.e. on the horizontal, into the adjacent roll. The rotational movement of the rolls is such, that the respective feeding rolls on each side of the horizontal plane rotate in the same direction and in the opposite direction to the feeding rolls on the opposite side of the horizontal plane, i.e. in the embodiment represented in FIG. 2 the lower rolls 17a, 17b rotate to the left and the upper ones 17a', 17b' rotate to the right. This arrangement and movement of the rolls in combination will ensure the complete removal of the adhesive tape (5, 5') from the first pair of lower and upper feeding rolls, 17a, 17a', since any residue remaining thereon will be removed by the movement of the second pair of lower and upper feeding rolls 17b, 17b'.

The material and design of the holding rolls 9a, 9a'; 9b, 9b' suitably are essentially similar to those of the feeding rolls 17a, 17a'; 17b, 17b'. Thus, they may comprise a number of SS 142346 stainless steel disks having a diameter of e.g. 15 mm and a thickness of 2 mm mounted on an axis of rotation at 3 mm intervals, i.e. at a separation of 5 mm between the centres of adjacent disks. Again, the disks preferably are knurled, i.e. the circumferential surface of each disk is serrated. The required double characteristics of having a good grip on the sample web 3 during the sequence of removal of the tester platens 10, 10' from the sample web 3 after performing a tensile strength test and being easily detached from the sample web 3 in view of resuming the feeding of the sample web 3 will thus be ensured.

The horizontal distance between the two pairs of holding rolls, 9a, 9a' and 9b, 9b' respectively, preferably will be as short as possible to allow for a maximum number of tests to be performed over a given length of the sample web 3 having regard to any other limiting factors, and to facilitate the removal of the tester platens 10, 10' from the adhesive tape 5, 5'. The lower limit for the distance is given by the width of the tester platens 10, 10' in the feeding direction. In the embodiment of the example, the horizontal distance between the centres of the two pairs of holding rolls, 9a, 9a' and 9b, 9b', is 66 mm, leaving a space of 51 mm horizontal width on the feeding direction of the sample web 3.

The purpose of the deflection rolls 8, 8' is to guide the double-sided pressure-sensitive adhesive tape 5, 5' onto the sample 2 of paper or board to be tested, so as to form the sample web 3. They thus do not need to fulfill the double requirement of good grip and easy detachability as discussed herein above, but rather should be devised so as to give a minimum of adherence with the adhesive tape 5, 5'. As an example, to suit such a purpose the deflection rolls 8, 8' may be formed of aluminium rolls having a diameter of 30 mm, anodized on at least that part of their surface which is to come in contact with the adhesive tape 5, 5' and being knurled. The knurling will provide a small surface area in contact with the adhesive tape 5, 5', the anodizing providing smoothness. The two features in combination act to minimize adherence.

Another possible design for the deflection rolls 8, 8' would be as stainless steel rolls having a diameter of e.g. 30 mm and, on at least that part of their surface which is to come in contact with the adhesive tape 5, 5', wearing a deposit of tungsten carbide particles and an outer coating of silicone rubber. The particles of tungsten carbide will provide a small surface area in contact with the adhesive tape 5, 5' whereas the silicone rubber coating will prevent adherence of the adhesive tape 5, 5' to the surface of the deflection rolls 8, 8'.

The pressure-sensitive adhesive tape 5, 5' suitable for use in the method and device of the invention is double-sided pressure-sensitive and coated on at least one side with a protective liner, i.e. release paper. More details as to the required properties thereof may be found in the description of the selected testing standard, such as those referred to herein above. As an example, a suitable, commercially available adhesive tape is Scotch Tape 410™ sold by 3M.

As noted above, the device of the invention is suitable for measuring the z-directional tensile strength of a paper or board by a method conforming with the SCAN P80:98 standard. When used according to this standard, it essentially is applicable to papers and boards having a grammage exceeding 60 g/m$^2$ and a z-directional tensile strength less than approximately 600 kN/m$^2$, as specified in said standard. Other parameters, such as the compression force used on the tester platens, the dwell time, the surface area and material of the tester platens may be found in said standard when this will be published.

However, the device of the invention is not limited only to the use according to said standard, but is equally applicable for measuring the z-directional tensile strength of a paper or board according to any other standard of similar principle, by modifications of the relevant parameters, easily performed by a person skilled in the art.

The usual practice in a paper mill is to perform sampling from each full jumbo roll leaving the paper or board machine. Such a jumbo roll may be 40 tons in weight and typically is produced in less than an hour. Specimens are taken from the last layers of paper or board on the jumbo roll and conditioned in the paper mill laboratory at standard temperature and humidity conditions, e.g. 23° C. temperature and 50% relative humidity. After a conditioning period of ½–1 hour, the specimen is cut into test pieces of dimensions suitable for the tensile strength testing device and number of tensile strength tests to be performed. As an example, with the device of the invention, a test piece having a width of 100 mm and a length of 350 mm may be suitable for performing 5 tensile strength measurements according to the method of the invention.

In performing quality controls of various characteristics of a paper or board, a usual practice is to take test pieces originating from several locations on the width of the web of paper or board, e.g. one test piece for 5 tests from the operator (front) side, one test piece for 5 tests from the middle and one test piece for 5 tests from the drive side of the web. The test data then may be averaged within each one of these three groups, giving three average values which will provide an indication of the uniformity of the measured characteristics over the width of the web.

In the method of the invention, the three test pieces originating from a jumbo roll, one test piece from the operator side, one from the middle and one from the drive side thereof, may be patched together and introduced into the testing device as one sample, e.g. three test pieces of 350 mm length each will be patched together to a sample of 1050 mm length.

To start a series of tensile strength tests by use of the device of the invention, the operator either selects a number of testing parameters at the computer, or retrieves a preexisting selection of parameters, e.g. as identified by a program number.

One parameter to be selected or which has been previously selected in the case of a preexisting program, is the feeding length of the sample web between each measuring sequence. The minimum length is set by the distance separating the holding rolls 9a, 9a' and 9b, 9b'. In order to minimize the consumption of adhesive tape 5, 5' one generally will select this distance as the value for the feeding length. E.g., by a distance of 66 mm separating the holding rolls 9a, 9a' and 9b, 9b', the minimum feeding length would be 66 mm. However, for some qualities of material, e.g. those having a substantial thickness and flexural rigidity, one might have to select a greater feeding length between each measuring sequence, since the delamination of a sample of such a material may spread over a substantial area, so that too small a distance separating the successive test areas would lead to the results of all of the tests, except the first one, of a series on a sample being biased. To avoid this, a feeding length of 100 mm–200 mm might then be necessary between each test area. This minimum necessary feeding length may easily be determined by first performing the tensile strength test on separate test pieces of the material, and then on one and the same test piece with a decreasing value for the feeding length between the test areas until, for a given feeding length, an influence from the preceding test can be seen on the test value. The threshold for the minimum necessary feeding length then has been crossed, and the selected feeding length preferably should exceed this last value by at least 50% to be sure not to have any biasing influence of the outlined kind.

Having performed the program selection, the sample of paper or board is installed on the feeding table and is given an identification number by the computer keyboard. The start command next may be given, the entire series of testing then being performed in a fully automatized way. The results obtained in general range from 60 kPa to 600 kPa in correspondence with the qualities of paper or board which are generally tested for the z-directional strength.

An example of the use of a device of the invention in a method of the invention will now be described.

EXAMPLE

The tested material is a liquid carton board having a grammage of 186 g/m². This is a quality frequently used in the production of packages such as milk cartons.

The testing is performed according to the proposed SCAN standard, referred to herein above.

A selection of parameters and values thereof, as stored in a program for the testing of the above type of material by use of the above standard or as entered by the operator at the computer keyboard before performing a testing cycle, are those given in the following table I.

TABLE I

| | |
|---|---|
| Test area | 10 cm² |
| Compression force[a] | 3000 N |
| Compression dwell time[a] | 6 s |
| Stroke speed[b] | 3 |
| N ° of tests / test piece | 5 |
| N ° of test pieces[c] / sample | 3 |
| Length of each test piece | 350 mm |
| Feeding length between each testing | 66 mm |
| System of Units | SI |
| Form of presentation of data output | average values |
| Standard deviation (y/n) | yes |

TABLE I-continued

| | |
|---|---|
| Coefficient of variation (y/n) | yes |
| Destination of output data | main computer |

Notes:
a - according to the proposed SCAN standard
b - The stroke speed, i.e. the speed of movement of the tester platens, is selected as a function of the expected tensile strength of the tested material, and should be such as to result in the break of the test piece within 3 ± 2 seconds.
Stroke speed 1 is selected for an expected tensile strength of 60–300 kPa; stroke speed 2 is selected for an expected tensile strength of 150–450 kpa; stroke speed 3 is selected for an expected tensile strength of 300–600 kPa.
c - Taken from the operator side, the middle and the drive side of the web of paper or board.

By the method and device of the invention, most of the manual sources of errors have been eliminated. This will result in an enhanced accuracy of the measured values, e.g. coefficients of variation typically ranging from 2% to 4%, which is far better than those generally obtained in the manual methods of the state of the art.

Moreover, the elimination of manual operation of the tensile strength tester platens by the method of the invention will result in a substantially reduced risk of contamination of said platens, such as by hand grease. Accordingly, the platens will have to be cleaned only at very large intervals of use, such as e.g. after every 1000 to 5000 tests. This should be compared with the cleaning requirements in the method of the state of the art, where cleaning by use of a solvent on a theoretical minimum according to e.g. the TAPPI standard has to be performed on every new day of testing, but in practice often has to be performed much more frequently.

What is claimed is:
1. A method of measuring z-directional tensile strength of a sample (2) of paper or board in a direction perpendicular to a surface thereof, comprising:
   adhering double-sided pressure-sensitive adhesive tape (5, 5') to two opposite surfaces of the sample (2) so as to obtain a sandwich structured sample web (3);
   bringing on each of the two opposite surfaces of the sample web (3), a tensile strength tester platen (10, 10') in contact with a free surface of the double-sided pressure-sensitive adhesive tape (5, 5');
   fastening, on each of the two opposite surfaces of the sample web (3), the tensile strength tester platen (10, 10') to the free surface of the double-sided pressure-sensitive adhesive tape (5, 5');
   pulling apart the tensile strength tester platens (10, 10') by use of a tensile force; and
   measuring the tensile force necessary to break the sample (2) in a plane between the two opposite surfaces of the sample;
   wherein a plurality of z-directional tensile strength tests are performed at separate locations on a continuous sample web (3).
2. The method of claim 1, characterized in that after performing a z-directional tensile strength test, the tester platens (10, 10') are detached from the sample web (3), the sample web (3) being retained by the grip of holding means (9a, 9a'; 9b, 9b').
3. The method of claim 2, characterized in that after detaching the tester platens (10, 10') from a test area of the sample web (3) on which a z-directional tensile strength test has been performed, a following test area of the sample web (3) is fed into a space between the tester platens (10, 10') for performing a further z-directional tensile strength test on said following test area.

4. The method of claim 1, characterized in that the sample (2) of paper or board comprises a sequence of several test pieces attached to each other.

5. A device (18) for measuring z-directional tensile strength of a sample (2) of paper or board, comprising:
- means (4, 4') for delivering double-sided pressure-sensitive adhesive tape (5, 5') provided with protective liner (7, 7') on at least one side;
- means (6, 6') for removing the protective liner (7, 7') from the double-sided pressure-sensitive adhesive tape (5, 5');
- means (8, 8') for applying the double-sided pressure-sensitive adhesive tape (5, 5') to two opposite sides of a sample (2) of paper or board giving a sandwich structured sample web (3);
- a tensile strength tester comprising a pair of tester platens (10, 10'); means (17a, 17a'; 17b, 17b') for feeding the sample web (3) into a space between the tester platens (10, 10'); and
- means (9a, 9a'; 9b, 9b') for holding the sample web (3), located on both sides of the tester platens (10, 10').

6. The device of claim 5, characterized in that: the sample web lies in a plane, and the tensile strength tester comprises means (13, 14, 15a, 15b, 16) for exerting a force on the tester platens (10, 10') in a direction perpendicular to the plane of the sample web (3) and means (12) for sensing the force exerted on the tester platens (10, 10').

7. The device of claim 6, characterized in that the means (13, 14, 15a, 15b, 16) for exerting force on the tester platens (10, 10') on one side of the plane of the sample web (3) comprises a pneumatic cylinder (13) and an opposite side thereof, pneumatic cylinders (14, 15a, 15b) and lifting yoke (16) coupled to one tester platen (10') through force sensor (12).

8. The device of claim 5 coupled to means (19, 20, 21) for controlling the device (18) and for receiving, storing and treating input as well as output data.

9. The device of claim 5, characterized in that: the sample web lies in a plane; the space between the tester platens includes a sample web test area having a center; one tester platen (10') at an end thereof proximal to the plane of the sample web (3) comprises a hemispherical bearing (11) having a rotation center located close to the center of the sample web (3) test area.

10. The device of claim 5, characterized in that the sample web lies in a plane, the means (4, 4') for delivering the double-sided pressure-sensitive adhesive tape (5, 5'), the means (6,6') for removing the protective liner (7, 7') from the double-sided pressure-sensitive adhesive tape (5, 5'), the means (8, 8') for applying the double-sided pressure-sensitive adhesive tape (5, 5') to the sample (2) of paper or board, giving a sandwich structured sample web (3), the means (9a, 9a'; 9b, 9b') for holding the sample web (3) and the means (17a, 17a'; 17b, 17b') for feeding the sample web (3) are located on each side of the plane of the sample web (3).

11. The device of claim 5 characterized in that the means (17a, 17a'; 17b, 17b') for feeding the sample web (3) comprises two pairs of feeding rolls located at an exit side of the tensile strength tester.

12. The device of claim 5, characterized in that the means (9a, 9'a; 9b, 9b') for holding the sample web (3) comprises two pairs of holding rolls suitable for being brought into and out of contact with the sample web (3).

13. The device of claim 5, characterized in that the means (8, 8') for applying the double-sided pressure-sensitive adhesive tape (5, 5') to the sample (2) of paper or board comprises a pair of deflection rolls located at an inlet side of the tensile strength tester.

14. The device of claim 8, characterized in that the means for controlling the device (18) and for receiving, storing and treating input as well as output data comprises microprocessors (19), a display unit (20) and a computer keyboard (21).

15. The device of claim 7, characterized in that one tester platen (10') at its end proximal to the plane of the sample web (3) comprises a hemispherical bearing (11) with its rotation center located close to a center of the sample web (3) test area.

16. The device of claim 15, characterized in that the means (4, 4') for delivering the double-sided pressure-sensitive adhesive tape (5, 5'), the means (6, 6') for removing the protective liner (7, 7') from the double-sided pressure-sensitive adhesive tape (5, 5'), the means (8, 8') for applying the double-sided pressure-sensitive adhesive tape (5, 5') to the sample (2) of paper or board, giving a sandwich structured sample web (3), the means (9a, 9a'; 9b, 9b') for holding the sample web (3) and the means (17a, 17a'; 17b, 17b') for feeding the sample web (3) are located on each side of the plane of the sample web (3).

17. The device of claim 16, characterized in that the means (17aa, 17a'; 17b, 17b') for feeding the sample web (3) comprises two pairs of feeding rolls located at an exit side of the tensile strength tester.

18. The device of claim 17, characterized in that the means (9a, 9a'; 9b, 9b') for holding the sample web (3) comprises two pairs of holding rolls suitable for being brought into and out of contact with the sample web (3).

19. The device of claim 18, characterized in that the means (8, 8') for applying the double-sided pressure-sensitive adhesive tape (5, 5') to the sample (2) of paper or board comprises a pair of deflection rolls located at an inlet side of the tensile strength tester.

20. The method of claim 3, characterized in that the sample (2) of paper or board comprises a sequence of several test pieces attached to each other.

* * * * *

UNITED STATES PATENT AND TRADEMARK OFFICE
CERTIFICATE OF CORRECTION

PATENT NO.    : 6,386,027 B1
DATED         : May 14, 2002
INVENTOR(S)   : Dennis Westin It is certified that error appears in the above-identified patent and that said Letters Patent is hereby corrected as shown below:

<u>Column 12,</u>
Line 59, delete "the grip of";

<u>Column 13,</u>
Line 30, after "(13) and" insert -- on --.

Signed and Sealed this

Twenty-second Day of October, 2002

Attest:

Attesting Officer

JAMES E. ROGAN
Director of the United States Patent and Trademark Office